United States Patent [19]

Bologna et al.

[11] Patent Number: 5,667,492

[45] Date of Patent: Sep. 16, 1997

[54] USE AND COMPOSITION OF AN ANTI-SEXUALLY TRANSMITTED DISEASES FORMULATION

[75] Inventors: William J. Bologna; Howard L. Levine, both of New York, N.Y.

[73] Assignee: Columbia Laboratories, Inc., Coconut Grove, Fla.

[21] Appl. No.: 319,495

[22] Filed: Oct. 7, 1994

[51] Int. Cl.$^6$ .................... A61M 31/00; A61F 6/06; A61K 31/79

[52] U.S. Cl. ............ 604/57; 604/307; 424/430; 424/78.25; 424/DIG. 14; 514/843; 514/967

[58] Field of Search ........... 604/307, 57; 424/430–435, 424/DIG. 14; 514/78.25, 843, 967

[56] References Cited

U.S. PATENT DOCUMENTS

| | | |
|---|---|---|
| 3,074,852 | 1/1963 | Mayron . |
| 4,286,593 | 9/1981 | Place et al. ............... 128/260 |
| 4,615,697 | 10/1986 | Robinson . |
| 4,983,393 | 1/1991 | Cohen ..................... 424/78.25 |
| 5,380,523 | 1/1995 | Digenis et al. ............ 424/78.25 |

FOREIGN PATENT DOCUMENTS

| | | |
|---|---|---|
| 0429156B1 | 9/1994 | European Pat. Off. . |
| 0431719B1 | 9/1994 | European Pat. Off. . |

OTHER PUBLICATIONS

Robert Berkow, M.D. et al., The Merck Manual 16th Edition, 1992, pp. 254–272.

Kreiss, J., et al., Efficacy of Nonoxynol 9 Contraceptive Sponge Use in Preventing Heterosexual Acquisition of HIV, Jul. 22/29, 1992, JAMA, vol. 268(4): 477–82.

Niruthisard, S. et al., Use of nonoxynol–9 and reduction in rate of gonococcal and chlamydial cervical infections, Jun. 6, 1992, Lancet, vol. 339: 1371–75.

Whaley, K.J., et al., Nonoxynol–9 Protects Mice Against Vaginal Transmission of Genital Herpes Infections, 1993, J.I.D., vol. 1993: 1009–11.

Pearce–Pratt, R., et al., Studies of Adhesion of Lymphocytic Cells: Implications for Sexual Transmission of HIV, 1993, Biology of Reproduction, vol. 48: 431–45.

Primary Examiner—Robert A. Clarke
Assistant Examiner—David Cho
Attorney, Agent, or Firm—Finnegan, Henderson, Farabow, Garrett & Dunner, L.L.P.

[57] ABSTRACT

The present invention provides a composition and use of a composition comprising a bioadhesive cross-linked polycarboxylic acid polymer formulation that enables the use of relatively low mounts of anti-STD infectants, such as N-9, to be used to prevent infection by STDs without causing the irritation to genital tissue that often accompanies higher doses of anti-STDs. The bioadhesive polymer maintains greater contact between the anti-STD agent and the infectant for a much greater period of time, enabling a lower concentration to act longer on the infectant, when compared to currently-available commercial applications containing N-9. Such delivery will enable a safe and non-irritating decrease in the risk of infection with STDs, including HIV.

8 Claims, 1 Drawing Sheet

USE AND COMPOSITION OF AN ANTI-SEXUALLY TRANSMITTED DISEASES FORMULATION

FIELD OF THE INVENTION

This invention relates to a bioadhesive polymer formulation for providing prolonged effect by relatively small concentrations of anti-STD agents, wherein the formulation comprises at least a cross-linked polycarboxylic acid polymer and an anti-STD agent.

BACKGROUND

Human Immunodeficiency Virus (HIV) is presumably the etiologic agent of Acquired Immunodeficiency Syndrome (AIDS). Many attempts have been and continue to be made to find mechanisms and agents to prevent or to cure an HIV infection, without much success.

Attention has been focused in part on measures that prevent infection by the virus. One method aimed at the heterosexual population has been the vaginal application of agents prior to and during intercourse, which agents are intended to inactivate the virus or remove its infectivity. An example is the use of surfactant- or detergent-based spermicides, exemplified by nonoxynol-9 ("N-9"), which have demonstrated activity against HIV and other sexually-transmitted diseases (STDs) at concentrations that would be expected to exist during intercourse after pre-coital application of the spermicide to the vagina. However, it is not necessarily a requirement that there be simultaneous presence of anti-STD and spermicidal activity. Currently available formulations of N-9 include jellies and sponges for spermicidal use in the vagina. However, at concentrations which may be effective in reducing the rate of gonococcal and chlamydial cervical infections, the rate of symptomatic irritation of the vagina and/or penis is substantially increased. In a study on the efficacy of the N-9 contraceptive sponge in preventing sexual acquisition of HIV by highly exposed women, N-9 was not effective in reducing infection by HIV, but genital ulcers and vulvitis occurred with substantially increased frequency.

It therefore is of interest to use delivery systems for anti-STDs that maintain contact between the anti-STD and the infective agent without harming host or partner tissue.

Relevant Literature

N-9 has been shown to be effective at inhibiting several sexually transmitted diseases, including AIDS, gonorrhea, chlamydia and trichomonal infections, syphilis and genital herpes. See, e.g., Niruthisard, S., et al., *Lancet*, 339: 1371 (1992).

Vaginal application of a commercially available contraceptive jelly containing 5% N-9 has been shown to be effective in preventing vaginal transmission of herpes simplex virus type 2 (HSV-2) infections in mice. Whaley, K. J., et al., *J. Infect. Diseases*, 168:1009, 1010–11 (1993). Dextrans and the carageen types of polysaccharides have been shown to have an anti-HIV potential. See, e.g., Pearce-Pratt, R. et al., *Bio. Reprod.*, 48:431,432 (1993).

The efficacy of a formulation based on a cross-linked polycarboxylic acid polymer for moisturization of skin or mucous membranes, such as vaginal tissue, is described in Robinson, J. R., European Patent Applications Serial Nos. 90300327.5 and 90300340.8.

SUMMARY OF THE INVENTION

The present invention is related to a method and drug delivery formulation for administration of anti-STD agents at a therapeutic concentration without substantial effect on host tissue, by potentiating the activity of the anti-STD and thereby facilitating its application in a substantially lower concentration. The invention is based upon use of a formulation which includes a bioadhesive cross-linked polycarboxylic acid polymer to deliver an anti-STD agent locally to a mucosal surface of potential exposure to an STD infectant, most typically a mucosal surface in a host body cavity such as the vagina or rectum. The method finds use in the prevention of infection of the host by STD agents.

BRIEF DESCRIPTION OF THE DRAWING

In FIG. 1, the data points for N-9 are represented by squares, and the data points for F-Po/N9 are represented by triangles.

DETAILED DESCRIPTION OF THE INVENTION

Figure 1:
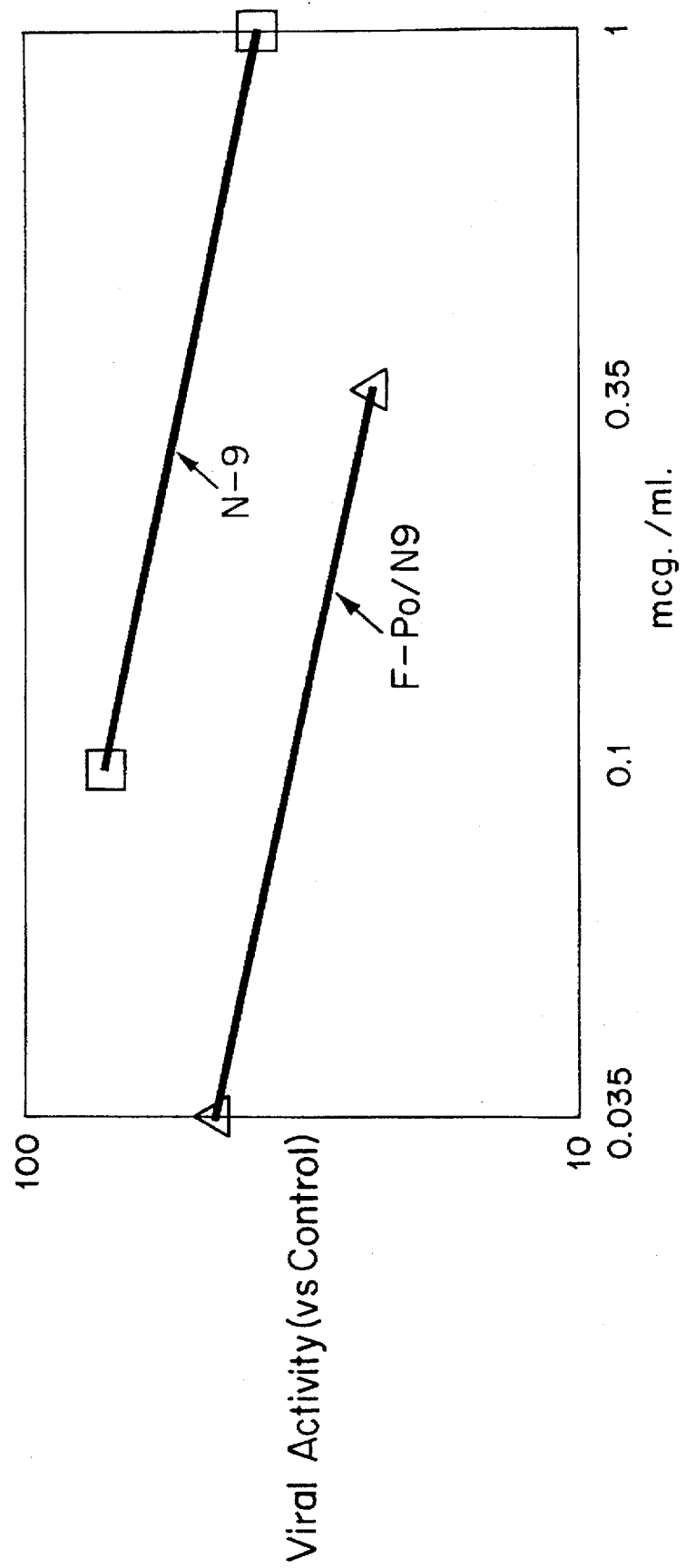
FIG. 1 illustrates the comparative virucidal effects, in vitro, of N-9 alone and a formulation which includes N-9 and polycarbophil (F-Po/N9), as described in further detail at Example 1. This log graph clearly demonstrates the potentiation of the antivirucidal effects of N-9 by the present invention, as measured by the reduction in the number of syncytia produced. As illustrated by FIG. 1, nonoxynol-9 alone, at concentrations of 1 and 0.1 µg/ml, reduced viral infection to 36% and 72% of that otherwise exhibited by the HIV viral suspension described below in Example 1. However, when the virus was contacted instead by F-Po/N9, the N-9 concentrations of only 0.35 and .035 µg/ml limited the viral infection to 23% and 47% of the HIV viral suspension.

The present invention comprises the use of a drug formulation based upon a delivery agent formulation comprising a cross-linked polycarboxylic acid polymer and an anti-STD agent, to deliver the anti-STD, for example N-9, to mucosal surfaces, particularly in a body cavity, to provide local concentrations of any anti-STD which are sufficient to inhibit or prevent infection by an STD, while substantially decreasing local tissue irritation and side effects often associated with formulations of anti-STD agents.

The use of a cross-linked polycarboxylic acid polymer in combination with an anti-STD agent offers several advantages over use of the anti-STD agent alone. Such polymers potentiate the anti-STD effect of the anti-STD by maintaining contact with the host body cavity tissue and infected tissues or cells, and thus prolonging the interaction between the anti-infectant component and the infectant for a greater time. As a result, a lower concentration of the STD component can be used to achieve anti-infectant activity. At such a lower concentration, the degree and amount of side effects and epithelial irritation caused by the anti-STD agent is substantially reduced. The bioadhesive polymeric system has the advantage of being held in a body cavity such as the vagina for relatively long periods of time, i.e., as much as 48 to 72 hours or longer, whereas most drug delivery systems are sloughed off the vaginal walls in less than four hours. The polymer holds the anti-infectant agent and slowly releases it over time. The drug delivery system allows for direct contact with any sperm and/or infectant introduced through sexual intercourse, or present in the vaginal or penile secretions prior to intercourse. The delivery system can deliver sufficient anti-infectant to effectively reduce the chance of infection with substantially lower frequency of counter-productive irritation to the genital tissues.

The decrease in the irritation to body cavity mucosal surfaces or to other epithelial tissue encourages more faithful use of the agent resulting in a more effective prevention of STD and/or pregnancy. Unlike most products, which are based on lubricants, the base formulation of the present invention is a moisturizer, further promoting comfort. Also, the effective use of lower concentrations enables a lower amount of N-9 to be used per dose. Another benefit of the present invention is that its compositions may be fabricated with relative ease. Yet another benefit of the present invention is that its compositions may be easily administered without requiring any sponge or other device which must be physically inserted and left in place, and then removed from the site of activity at some later time. A smaller quantity of the formulation is needed, facilitating neater application with less chance of leakage and increased compliance of proper application. Another benefit of the present invention is that it allows the user to apply the product more than just a few minutes before sexual intercourse without significant loss of efficacy of the formulation, further promoting increased compliance.

The polymer used in the drug delivery formulation is a cross-linked polycarboxylic acid polymer wherein at least eighty percent of the monomers of which the polymer is comprised contain at least one carboxyl functionality. The cross-linking agent should be present at such an amount as to provide enough bioadhesion to allow the system to remain attached to the target epithelial surfaces for preferably a period of twenty-four to forty-eight hours. Such results may be measured clinically over various periods of time, by testing samples of the vaginal vault for concentration of the anti-STD agent or for pH reduction due to the continued presence of the polymer, or both.

This level of bioadhesion is usually attained when the cross-linking agent is present at about 0.1 to 6.0 weight percent of the polymer, with about 1.0 to 2.0 weight percent being preferred, as long as the appropriate level of bioadhesion results. Bioadhesion can also be measured by commercially available surface tensiometers utilized to measure adhesive strength. Suitable cross-linking agents include divinyl glycol, divinylbenzene, N,N-diallylacrylamide, 3,4-dihydroxy-1,5-hexadiene, 2,5-dimethyl-1,5-hexadiene and similar agents.

The basic drug delivery system formulation of the present invention—the cross-linked polycarboxylic acid polymer formulation to which is added the anti-STD agent—is generally described in U.S. Pat. No. 4,615,697 to Robinson (hereinafter "the '697 patent"), which is incorporated herein by reference. A preferred polymer for use herein is Polycarbophil, U.S.P., which is commercially available from B.F. Goodrich Specialty Polymers of Cleveland, Ohio under the trade name NOVEON®-AA1. The United States Pharmacopeia, 1995 edition, United States Pharmacopeial Convention, Inc., Rockville, Md., at pages 1240–41, indicates that polycarbophil is a polyacrylic acid, cross-linked with divinyl glycol.

Other useful bioadhesive polymers that may be used in the present invention are mentioned in the '697 patent. For example, these include polyacrylic acid polymers cross-linked with, for example, 3,4-dihydroxy-1,5-hexadiene, and polymethacrylic acid polymers cross-linked with, for example, divinyl benzene.

These polymers should not be used in their salt form because this would decrease their bioadhesive capability. Such bioadhesive polymers may be prepared by conventional free radical polymerization techniques utilizing initiators such as benzoyl peroxide, azobisisobutyronitrile, and the like. Exemplary preparations of useful bioadhesives are provided in the '697 patent.

Additionally, the additives taught in the '697 patent may be mixed in with the cross-linked polymer in the formulation for maximum efficacy of the drug delivery system or for the comfort of the patient. Such additives include, for example, lubricants, plasticizing agents, preservatives, gel formers, binders, vehicles, coloring agents, taste and/or odor controlling agents, humectants, viscosity controlling agents and similar agents, and preferably have no substantial detrimental effect on the anti-STD and/or spermicide activity of the drug delivery formulation.

STD's that can be treated by N-9 include, but are not limited to, AIDS, gonorrhea, chlamydia and trichomonal infections, syphilis and genital herpes. Other anti-STD agents include, for example: other detergents/surfactants, such as octoxynol-9, chlorhexidine, and benzalkonium chloride, which are also generally effective against STDs; and anti-metabolites, such as AZT, or competitive binding inhibitors such as dextrans, all of which are generally most effective against viral STDs, such as HIV and genital herpes.

The anti-STD is mixed into the formulation, associating reversibly with the polymer. Upon application, the anti-STD leaches out of the formulation slowly over time, depending on the proportions and concentrations of the formulation components. Correct concentrations for particular STDs can be determined by testing and comparing the results of various concentrations of an anti-STD against a particular STD, in tests similar to those described below in Example 2.

| INGREDIENT | AMOUNT (Kg) |
| --- | --- |
| Nonoxynol-9 | 1.750 |
| Methylparaben | 0.090 |
| Sorbic Acid | 0.040 |
| Carbomer 934P | 0.250 |
| Polycarbophil | 0.500 |
| Glycerin | 5.000 |
| Mineral Oil | 2.500 |
| Hydrogenated Palm Oil Glyceride | 0.500 |
| Sodium Hydroxide | 0.0125 |
| Purified Water | 39.3575 |

Methylparaben and sorbic acid are preservatives, which may be substituted by any other approved preservative, such as benzoic acid or propionic acid.

Carbomer 934P is a gel former, which may be substituted by other gel formers including, but not limited to, carbomer 974, carbomer 980, methylcellulose or propylcellulose.

Glycerin is a humectant; alternative humectants include, for example, propylene glycol or dipropylene glycol.

Mineral oil and hydrogenated palm oil glyceride are lubricating agents; alternatives include, for example, any mineral oil or vegetable oil, such as canola oil, palm oil or light mineral oil.

Sodium hydroxide is simply a strong base for purposes of controlling the pH level; other bases commonly used for that purpose may be substituted.

General preparation involves hydration of the polymers, separate mixing of water-soluble ingredients (the "polymer phase") and oil-soluble ingredients (the "oil phase"), heating and mixing of the two phases, and homogenization of the mixture. All ingredients in this example are well known and readily available from suppliers known in the industry.

As an example, the polymer phase is prepared by dissolving the sorbic acid and methylparaben in purified water (along with an excess volume of about 3% of the intended volume of purified water, to account for evaporative losses), preferably at 75°–78° C. The solution is cooled, generally to room temperature, and the polycarbophil and Carbomer 934P are added. The polymers are hydrated by mixing for several hours, generally about 2–3 hours until a uniform, smooth, lump-free gel-like polymer mixture is obtained. When the polymers are completely hydrated, the nonoxynol-9 is added and mixed in, until uniform preparation is obtained.

The oil phase is generally prepared by melting together the hydrogenated palm oil glyceride, glycerin and mineral oil. The mixture is cooled to about 60° C., while the polymer phase is warmed to about the same temperature.

The oil phase is then added to the polymer phase, and the two phases are mixed thoroughly, producing a uniform, creamy whim product. Mix in sodium hydroxide to produce a pH of about 2.5–4.5, generally about 4. When the mixture has cooled, it is de-aerated. The resulting product is aseptic, because of the nature of the preparation and pH as well as the presence of preservatives.

As will be apparent to those skilled in the art, the composition of the formulation can be varied to control the effectiveness of a particular concentration of anti-STD agent. For example, the concentration of the bioadhesive polymer can be adjusted to provide greater or lesser bioadhesion. The viscosity of the gel can be varied by varying the pH or by changing the concentration of the polymer or gel former. The relative concentrations of the oils compared to the water can be varied to modulate the release rate of the anti-STD from the drug delivery system. The pH can also be varied to affect the release rate or bioadhesiveness of the formulation.

The drug delivery system may be delivered to the body cavity such as vagina or rectum in a variety of fashions as are known in the art, e.g., plunger, douche, suppository or manually. A preferred method of delivery is using the device described in U.S. Pat. No. Des. D345,211, which disclosure is incorporated herein by reference. This device is an oblong hollow container, with one end capable of being opened and the other end containing most of the composition to be delivered and capable of being squeezed. Such devices allow for pre-measurement of the amounts of polymer and drug to be delivered in a sealed container which may be used relatively easily. The containers also maintain the drug and polymer in a sterile environment until use. Upon use the container is opened and the open end is inserted into the body cavity by the host or his/her partner, while the other end is squeezed to expel the contents of the container into the body cavity. Accordingly, F-Po/N9 is preferably provided as a kit, which includes at least one single dose delivery device. The kit can include a single dose or multiple doses of the formulation.

In a preferred formulation, F-Po/N9 is prepared using polycarbophil, U.S.P., purchased from B.F. Goodrich Specialty Polymers, as the polymer in about a 1% gel formulation which is adjusted to a pH of about 2.5–4.5 with, for example, sodium hydroxide, yielding a viscosity of 40,000 to 90,000 cps. The anti-STD agent is N-9, preferably added at about 2 to 5 weight-percent, and optimally at about 3.5 weight-percent, of the total composition. The dosage of such composition would be preferably about 1 to about 2.5 g., most preferably about 1.5 g., total weight of formulation, calculated in combination with the concentration of N-9 to yield preferably about 50 to 55 mg, and most preferably about 52.5 mg., of N-9 per dosage. Ideally, the subject should apply one dosage before each act of sexual intercourse, primarily to reinforce faithful use of the formulation at an appropriate frequency. The applicator used is preferably disposable and provides accurate amount of delivery, such as the applicators described in U.S. Pat. No. Des. D345,211 and U.S. design patent application Ser. No. 29/019,916, providing delivery of the desired dosage of formulation at at least about ±5% accuracy.

The examples described and discussed herein are intended to be illustrative of the present invention but not limiting. Numerous variations and modifications may be effected without departing from the true spirit and scope of the novel concepts of the present invention.

EXAMPLES

Example 1

Comparison of Effects of N-9, Polycarbophil Formulation and Polycarbophil Formulation With N-9 on Viral Suspension of HIV LAV1 BRU Clone Nonoxynol-9, a 2% polycarbophil formulation (F-Po) and a formulation with about 3.5% N-9 and about 1% polycarbophil (F-Po/N9) were tested for activity on HT4LacZ cellular infection by a HIV LAV1 BRU retrovirus clone. The formulations were prepared according to the description discussed above, except that the F-Po was prepared with about 2% polycarbophil, no N-9 and about a 1% concentration of Carbomer 934P, rather than 0.5%, and the difference (2%) was made up with additional water.

A vital blank was used as control, and AZT was used for a positive control. Each formulation was set up as an aqueous suspension of a particular concentration. 500 µl. aliquots of viral suspension were separately mixed with 50 µl. of each of the test solutions. After 30 minutes, 55 µl. of each of these mixtures were tested directly on HT4LacZ cells in a well also containing DEAE dextran. During the culturing period, the virus supplies the tat gene missing in HT4LacZ cells, leading to LacZ gene transactivation coding for β-galactosidase, indicated by a histochemical coloration. After 72 hours of culturing, infection is stopped by addition of a fixator for ten minutes. After two PBS washes, the colorant is added for ninety minutes. After syncytia (giant multi-nucleated cells, formed by many cells fusing together when infected with HIV) outbreak, the colorant is replaced with water. Observation is performed with an optical microscope, yielding the following results in Table 1:

TABLE 1

ANTI-HIV ACTIVITY OF F-PO/N9, F-PO AND N-9

| Substance | Final Conc. (µg/ml) | Syncytia per well; 2–4 wells | Total # Syncytia | Avg. # Syncytia per well | Percent Reduction |
| --- | --- | --- | --- | --- | --- |
| Viral Reference | — | 16, 15, 17 | 48 | 16 | φ |
| N-9 | 1.0 | 6, 5, 7, 5 | 23 | 5.75 | 64 |
| N-9 | 0.10 | 12, 11, 13, 10 | 46 | 11.5 | 28 |
| F-Po/N9 | 0.35 | 4, 3, 4, 4 | 15 | 3.75 | 77 |
| F-Po/N9 | 0.035 | 8, 7, 9, 6 | 30 | 7.5 | 53 |
| F-Po | 200 | 13, —, 11, — | 24 | 12 | 25 |
| AZT | $(10^{-5}M)$ | 0, 0, | 0 | 0 | 100 |

In Table 1, φ percent reduction corresponds to 100% infection by the reference virus, and 100% reduction to the total lack of syncytia in wells for a given formulation. While the control positive AZT demonstrated 100 % effectiveness against the virus (0 syncytia produced), the viral reference produced an average of 16 syncytia per well. N-9 alone, at final concentrations of 0.1 and 1 μg/ml, respectively, provided 28% and effectiveness against infection as measured by decreases of syncytia produced. In comparison, F-Po/N9, at final N-9 concentrations of only 0.35 and .035 μg/ml, produced 77% and 53% effectiveness against infection, respectively. F-Po, at a final polycarbophil concentration of 200 μg/ml, yielded a 25% decrease in infection rate. Clearly, the N-9 in the polycarbophil formulation with N-9 exhibited substantially greater concentration-effectiveness than N-9 alone, as illustrated by FIG. 1.

Example 2

Comparison of Anti-HIV Activity of F-Po/N9 and F-Po

Anti-HIV effects were compared for F-Po/N9 and F-Po, the same formulations as in Example 1 above. This study used increase in p24 core protein from MT2 cells, in cell culture fluid using ELISA, as an indication of viral replication.

To evaluate the effect of F-Po/N9 on HIV replication, samples of virally-exposed MT2 cell culture fluid were serially diluted and tested for increase in p24 antigen The absorbance for each dilution of virus was plotted, and the 50% endpoint calculated. In this study, the 50% endpoint is the dilution of virus which would give an absorbance of 1.000 at 450 nm. wavelength.

The viral inoculum, using HIV-IIIB produced by co-cultivation of cell lines CEM and CEMCBL1, was mixed with an equal volume of the formulations for 1 minute at room temperature. Then, the mixture was added to 800 μl of isotonic acetate buffer, at a 1:10 dilution. 100 μl of this mixture was then added to $2 \times 10^6$ cells in a small tissue culture flask. If necessitated by the concentration, the mixture is diluted before inoculating the cells, to reduce the final concentration of the products in contact with the cells to less than 1 μg/ml. As a control, virus was mixed with buffer, held for one minute, and similarly diluted. After 1 hour of incubation at 37° C. to allow the virus to adsorb to the cells and for infection to occur, fresh tissue culture medium was added to the flask to bring the volume to 11 ml. The contents were gently mixed, and 1 ml of cell culture removed and titrated for infectious virus, using the microtitre test, and then stored at −20° C. until testing for p24 antigen. The flask was then incubated at 37° C. for up to 14 days, during which time 1 ml samples of cell culture fluid were removed, titrated and stored for p24 testing.

All samples were tested for p24 antigen by an indirect ELISA, to measure viral replication with time. Inactivated virus would demonstrate a constant level of p24 antigen, indicative of no replication taking place.

F-Po reduced the amount of HIV replication by about a third, at polycarbophil concentrations ranging from 2.0 mg/ml to 0.0002 mg/ml. F-Po/N9 almost totally inactivated HIV replication at a concentration of 100 mg/ml (3.5 mg/ml of N-9), and reduced HIV replication by about a third at concentrations of 0.10 to 10 mg/ml (0.0035 to 0.35 mg/ml of N-9), and by under 20% at a concentration of 0.01 mg/ml (0.00035 mg/mi. of N-9).

Example 3

Irritation and Convenience Clinical Trials For Polycarbophil Formulation with N-9

F-Po/N9, as formulated above with about 52.5 mg. per application, was compared to the TODAY contraceptive sponge, a commercial contraceptive sponge product with 1 g. of nonoxynol-9 per application, and CONCEPTROL contraceptive gel, a commercial vaginal contraceptive gel product containing 100 mg. per application of nonoxynol-9. In this study, one application was made each day by each of 31 female subjects, for seven days consecutively for each product, with a 21-day "washout" period in between products. Each application of the sponge product was left in place for 24 hours.

Blood samples were taken at various times to measure serum concentration of N-9. None of the products produced any significant serum concentrations for any of the subjects. Examinations were also conducted by an investigator to note the existence and degree of any vaginal or cervical irritation, including redness, petechiae, ulceration, infection, punctation, mosaic, leukoplakia, nonstaining squamous epithelium, columnar epithelium or white epithelium. A significantly higher average incidence of irritation was observed with CONCEPTROL contraceptive than with F-Po/N9, and a significantly higher intensity of irritation was observed with the Today® sponge than with F-Po/N9.

In a separate study, subjective comments regarding relative irritation and discomfort were solicited from nineteen female subjects using, at different times, F-Po/N9 and the TODAY contraceptive sponge. Overall preference of one product over the other was also requested, from 18 of the subjects. The products were used daily for a period of ten days each. F-Po/N9 has a unit dosage of about 52.5 rag. of N-9, while the TODAY contraceptive sponge product contains a unit dosages of 1 g. of N-9. F-Po/N9 generally was preferred by the subjects over the sponge product.

In order to demonstrate anti-STD effectiveness of the present invention in vivo for identification or concentration of particular anti-STD agents or particular STD's, clinical studies could be undertaken, for example, in a manner similar to those conducted and described in Kreiss, J., et at., J.A.M.A., 268(4):477–82 (1992) and Niruthisard, S., et al., Lancet, 339:1371–75 (1992). In each of these studies, previously-uninfected subjects used nonoxynol-9 in one form and formulation or another, over a period of time during and after which they were carefully monitored for compliance of application and for various STDs. The disclosures of these reported studies are incorporated herein by reference; variations on these studies for use with particular parameters will be obvious to those skilled in the art.

For example, F-Po/N9 as formulated above or otherwise could be administered on a daily basis to a test population, in parallel to a control blank, after thorough initial screening for non-infected individuals. Careful monitoring and testing will disclose the relative infection rate for a particular STD, and thus the effectiveness of that particular formulation of F-Po/N9.

N-9 is one substance that has been demonstrated to neutralize HIV and lymphocytes containing HIV. However, it is generally used at concentrations so great —usually 100–400 mg. per application, and as much as 1 g. per application—as to cause a substantial degree and number of side effects, including, at times, cellular lysis of host cells. Such injury may result in an increased susceptibility to infection, in effect counteracting at least in whole or part the anti-infectant activity of the N-9. The present invention should allow, for example, the use of a product containing only about 52.5 g of nonoxynol-9, in a formulation using polycarbophil as the polymer, without compromising the protection afforded by N-9 against infection with HIV and other STDs, or the effectiveness of the preparation as a spermicide. Further, the polymer itself also demonstrates anti-HIV activity. This may be based on the demonstrated ability of polyanions to inhibit the attachment of the HIV to susceptible cells, presumably by an electrostatic screening. It is thus clear that the present invention provides a formulation which potentiates the anti-HIV activity of N-9.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention how having been fully described, it will be apparent to those skilled in the art that many variations and modifications can be made thereto without departing from the spirit or scope of the appended claims.

What is claimed is:

1. A method of delivering N-9 as an anti-HIV agent to a female subject comprising inserting a bioadhesive cross-linked polycarboxylic acid polymer formulation with N-9 into the vagina, wherein the formulation releases N-9 at a rate sufficient to demonstrate anti-HIV activity for at least about twenty-four hours without significant causation of irritation to the local epithelial tissue.

2. The method according to claim 1 wherein the rate of release is sufficient to demonstrate anti-HIV activity for at least about forty-eight to seventy-two hours without significant causation of irritation to the local epithelial tissue.

3. The method according to claim 1 wherein the polymer is polycarbophil.

4. The method according to claim 3 wherein about 52.5 mg. of N-9 is inserted into the vagina.

5. The method according to claim 4 wherein the formulation includes at least one adjuvant.

6. The method according to claim 5 wherein the formulation is a gel-like product which is provided with or in a single- or multi-dose disposable applicator.

7. A method of delivering N-9 as an anti-HIV agent to a female subject comprising inserting a bioadhesive cross-linked polycarboxylic acid polymer formulation with N-9 into the vagina, wherein the formulation releases N-9 in an amount sufficient to demonstrate anti-HIV activity for at least about twenty-four hours without significant causation of irritation to the local epithelial tissue.

8. The method according to claim 7 wherein the anti-STD activity is demonstrated for at least about forty-eight to seventy-two hours.

* * * * *

UNITED STATES PATENT AND TRADEMARK OFFICE
CERTIFICATE OF CORRECTION

PATENT NO. : 5,667,492
DATED : September 2, 1997
INVENTOR(S) : Bologna et al.

It is certified that error appears in the above-identified patent and that said Letters Patent is hereby corrected as shown below:

On the Title page, Item [75], please correct to read as follows:

Inventors: William J. Bologna, New York, NY; Howard L. Levine, Oceanside, NY.

On the Title page, Item [57], in the Abstract, line 4, "mounts" should read --amounts--.

Signed and Sealed this

Thirtieth Day of December, 1997

Attest:

BRUCE LEHMAN

Attesting Officer

Commissioner of Patents and Trademarks